United States Patent
Marron

(10) Patent No.: US 6,245,114 B1
(45) Date of Patent: *Jun. 12, 2001

(54) ATHLETIC EQUIPMENT ATTACHMENT

(76) Inventor: Kathleen T. Marron, 9820 Hawkins Creamery Rd., Damascus, MD (US) 20872

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/177,108

(22) Filed: Oct. 22, 1998

Related U.S. Application Data

(60) Provisional application No. 60/062,698, filed on Oct. 23, 1997.

(51) Int. Cl.[7] ............................................. A61F 2/80
(52) U.S. Cl. ................................... 623/65; 623/33
(58) Field of Search ........................ 623/65, 63, 57, 623/32, 33, 34, 35, 61

(56) References Cited

U.S. PATENT DOCUMENTS

| | | | |
|---|---|---|---|
| 3,186,006 | * 6/1965 | Miller | 623/36 |
| 3,490,078 | * 1/1970 | Perez, Jr. | 623/65 |
| 3,747,128 | * 7/1973 | DeFilipo | 623/65 |
| 3,802,302 | * 4/1974 | Bengtson | 623/65 |
| 4,009,496 | * 3/1977 | Allen, III | 623/65 |
| 4,661,113 | * 4/1987 | Adkins | 623/65 |
| 5,464,444 | * 11/1995 | Farguharson et al. | 623/65 |
| 5,728,165 | * 3/1998 | Brown, Sr. | 623/33 |
| 5,800,572 | * 9/1998 | Loveall | 623/63 |

* cited by examiner

Primary Examiner—Bruce Snow
(74) Attorney, Agent, or Firm—Jacobson, Price, Holman & Stern, PLLC

(57) ABSTRACT

An athletic equipment attachment for use by persons having a stump arm, such as amputees and persons having congenital birth defects, is described and claimed. The inventive athletic equipment attachment includes a body having a top end with an adjustable opening configured to receive a person's stump arm, and a bottom end with connecting means for either removably or permanently connecting the attachment to the handle of a piece of athletic equipment, such as a field hockey stick, an ice hockey stick, a golf club or the like. The attachment can also be used as a rehabilitative tool or in connection with items for daily use, such as brooms or mops.

21 Claims, 7 Drawing Sheets

ATHLETIC EQUIPMENT ATTACHMENT

This application claims the benefit of Provisional No. 60/062,698 filed Oct. 23, 1997.

BACKGROUND OF THE INVENTION

1. Field of the Invention

The present invention relates to an athletic equipment attachment. More specifically, the invention relates to an athletic equipment attachment for use by persons missing part of a limb, such as an arm from amputation or a congenital birth defect.

2. Related Art

Athletic equipment attachments that connect to a prosthesis which in turn is attached to a wearer's arm and/or body are well known. For example, U. S. Pat. No. 4,661,113 to Adkins discloses an attachment which is attachable at one end to a handicapped arm or prosthesis and removably attached at its other end to a threaded stud secured in the handle end of an implement such as a golf club. The attachment includes an axially non-rotatable, universal pivot connection allowing versatile movement of the implement.

U.S. Pat. No. 4,357,717 to Puhl discloses an attachment configured to be connected to a prosthesis at one end and to a sports implement handle, such as a golf club handle, at its other end. The attachment includes a central section of resilient material that flexes upon swinging of the arm to produce a wrist-type whipping action.

U.S. Pat. No. 3,965,491 to Frenzel discloses a prosthetic device for holding golf clubs. The device includes an arm socket member which attaches to the upper arm and shoulder of an amputee. The arm socket member includes a threaded hole configured to receive a threaded shaft located at one end of a standard attachment for an arm socket member. The opposite end of the standard attachment has metal sleeves configured to receive the handle of a golf club.

These attachments are connected to a prosthesis which in turn is attached to the wearer's body through a complemental arrangement of body straps, and therefore tend to be bulky. Such attachments are not suitable for use with a field or ice hockey stick, because during such use a player typically carries the stick in one hand while running or skating. It is therefore desirable to provide an athletic equipment attachment which is quickly removably attached to the wearer's body. It is also desirable to provide an attachment which has an adjustable opening configured to receive the stump of a person's arm, so that the person may easily remove the stump from the opening and quickly reinsert the stump into the opening during play. It is further desirable to provide such an attachment which can be used with a variety of athletic equipment, including but not limited to field hockey sticks, ice hockey sticks, cricket bats and golf clubs.

SUMMARY OF THE INVENTION

The present invention provides an attachment for athletic equipment or any type of non-athletic equipment. For example, the attachment is suitable for use with a variety of equipment, including field and ice hockey sticks, cricket bats, golf clubs, et cetera. The attachment includes an adjustable top end configured to snugly receive the stump of a wearer's arm while allowing the wearer to easily remove and reinsert the stump in a supported position within the top end of the attachment during use, and a bottom end configured to receive the handle of a piece of athletic equipment.

The attachment has medical applications as a rehabilitation device for amputees and persons with congenital birth defects. For example, the attachment could be used in connection with weights for therapeutic applications. The attachment can also be adapted for use with various tools for everyday activities, such as household implements (for example, brooms, mops, dusters, vacuums), construction implements (for example, hammers, wrenches and other tools, axes, paint brushes) and garden and landscaping implements (for example, rakes, shovels, picks, hoes, scythes, tree pruners) and any other hand-held implements.

Because the attachment has an adjustable top end and is not attached to the wearer's body, the wearer may quickly remove and reinsert his/her stump during use. This is particularly important in field hockey, ice hockey and cricket applications, where players typically hold their stick or bat in one hand while running down a field or skating across ice. This also provides a psychological benefit, because some handicapped persons may prefer not to wear conventional prosthetic devices, which tend to be bulky and awkward, particularly when used in combination with an attachment for athletic equipment.

According to a first embodiment of the invention, the attachment is removably attached at its bottom end to the handle of the athletic equipment so that it can be removed from the equipment for interchangeable use with other pieces of equipment. For example, where the attachment is used for playing golf, it can be easily removed and attached to different clubs when the player wishes to change clubs.

As discussed above, the attachment can also be removably or permanently attached to weights or other tools, such as household implements, construction implements, garden and landscaping implements and any other hand-held implements, for rehabilitative and everyday use.

According to a second embodiment of the invention, the attachment is permanently attached at its bottom end to the handle of the athletic equipment to provide added strength and stability during use. This is particularly desirable when the attachment is used with a golf club or hockey stick.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which.

DETAILED DESCRIPTION OF THE PREFERRED EMBODIMENTS

Figure 1:
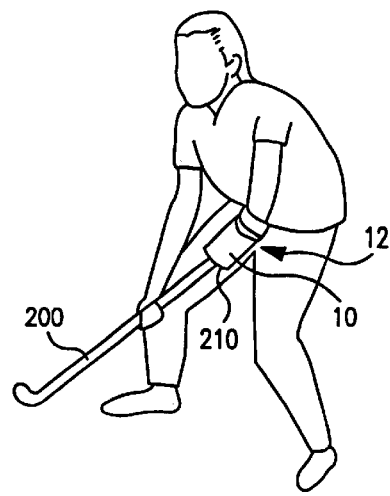
FIG. 1 schematically illustrates a person using the inventive athletic equipment attachment with a field hockey stick.

In describing preferred embodiments of the present invention illustrated in the drawings, specific terminology is employed for the sake of clarity. However, the invention is not intended to be limited to the specific terminology so selected, and it is to be understood that each specific element includes all technical equivalents which operate in a similar manner to accomplish a similar purpose.

The inventive athletic equipment attachment 10 can be attached at its bottom end 14 to a handle 210 of a piece of athletic equipment 200, such as a field hockey stick, an ice hockey stick, a golf club or a cricket bat, for use by a wearer who is missing part of an arm. As illustrated in FIG. 1, the stump of the wearer's arm is inserted into the top end 12 of attachment 10.

Figure 2:
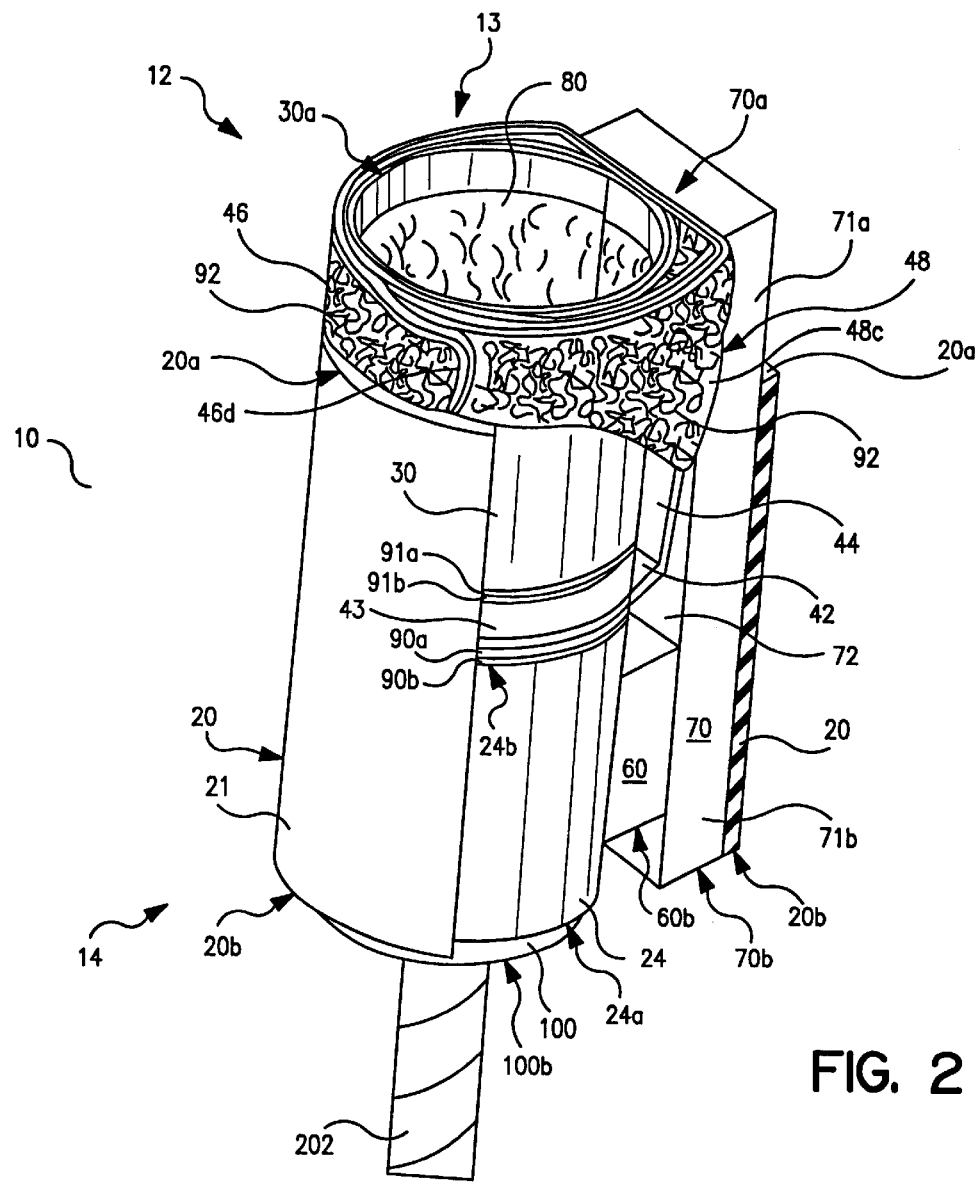
FIG. 2 is a cut-away perspective view of the inventive athletic equipment attachment.
Figure 3:
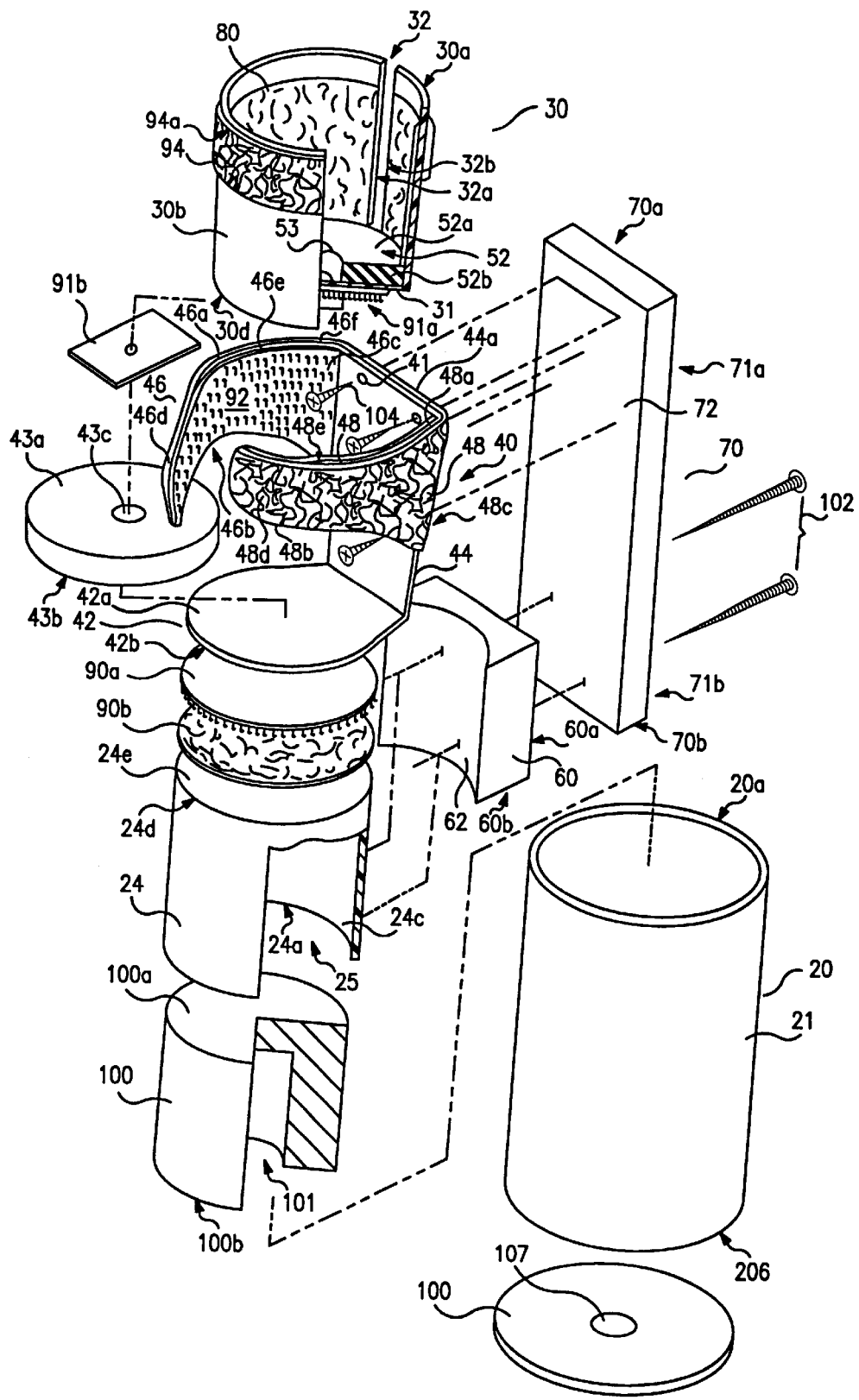
FIG. 3 is an exploded view of the inventive athletic equipment attachment.

As illustrated in FIGS. 2 and 3, attachment 10 has an adjustable top end 12 configured to receive the stump of a wearer's arm and a bottom end 14 which attaches to the handle 210 of a piece of athletic equipment 200. An outer protective cylinder 20 houses an inverted downwardly facing bottom cup 24, an upwardly-facing top cup 30 and an upwardly facing top cup holder 40 having adjustable first and second arms 46, 48.

Outer protective cylinder 20 is preferably formed from a cushioning material, such as foam rubber. It is hollow and preferably has an inner diameter of about 2½ to 2¾ inches and a height of about 4 to 4¼ inches. It is oriented vertically as shown in FIG. 2, with its top edge 20a facing upward and its bottom edge 20b facing downward. Inverted bottom cup 24 may be formed from any container, such as a cup, and is preferably made of hard plastic, such as polyvinyl chloride (PVC). Alternatively, bottom cup 24 may be made of any other suitable material. Bottom cup 24 preferably has a diameter of about 2¼ to 2⅜ inches and a height of about 2¼ to 2½ inches. It is oriented inside cylinder 20 as shown in FIG. 2, with its top rim 24a facing downward and lying flush against bottom edge 20b of cylinder 20 and its body extending upward into cylinder 20 so that its bottom end 24b faces upward and is located approximately halfway up the length of cylinder 20.

As an example, outer protective cylinder 20 and inverted bottom cup 24 may be formed from a foam drink holder including an outer foam rubber cylinder housing a removable cup insert. Such foam drink holders are commercially available from various local beverage stores. First, the cup insert is removed from the foam rubber cylinder. The cup insert is used as inverted inner bottom cup 24 by inverting the cup and inserting it through the opening of the foam rubber cylinder so that bottom cup 24 is oriented as shown in FIG. 2 and described above. The foam bottom of the foam drink holder is then removed in order to form the outer protective cylinder 20. The foam bottom of the foam drink holder is used as the top cup insert 52, discussed below. The foam bottom of another foam drink holder may also be used as the cup holder insert 43, discussed below.

Any portion of bottom cup 24 which extends beyond bottom edge 20b of outer protective cylinder 20 should be removed, for example by trimming bottom cup 24 with a hacksaw. Bottom cup 24 is inverted and inserted into cylinder 20 so that it is oriented as shown in FIG. 2 and described above, with its rim 24a facing downward and lying flush against bottom edge 20b of cylinder 20 and its body extending upward into cylinder 20 so that its bottom end 24b faces upward and is located approximately halfway up the length of cylinder 20.

Next, top cup 30 and top cup holder 40 are assembled. Cup holder 40 may be formed from any container having an adjustable neck. As an example, cup holder 40 may be formed from an adjustable plastic car cup holder having a non-connecting front collar with flexible arms, such as car cup holders commercially available from Rubber Queen (No. 5121) "Cup-A-Can Holder." Cup holder 40 is preferably made of plastic. Alternatively, cup holder 40 may be formed from any other combination of suitable material.

With reference to FIG. 3, cup holder 40 has a planar bottom 42, a planar back 44 extending perpendicularly upwardly from bottom 42, and first and second adjustable arms 46, 48 extending outwardly from sides 44a, 44b of back 44. Preferably, top edges 46a, 48a of first and second arms 46, 48 are flush with top edge 44a of back 44. Where cup holder 40 is formed from a car cup holder as described above, any portion of the back of the car cup holder which extends upwardly past first and second arms 46, 48 should be removed, for example by trimming with a hacksaw, so that the top edges 46a, 48a of arms 46, 48 are flush with the top edge 44a of back 44 as illustrated in FIG. 3.

Bottom 42 of cup holder 40 is preferably planar and circular, with a diameter of about 2¼ to 2⅜ inches. Back 44 of cup holder 40 extends perpendicularly upwardly from bottom 42 and is preferably planar and rectangular with a height of about 3⅛, to 3¼ inch and a width of about 2½ to 2⅝ inch. Arms 46, 48 extend outwardly from back 44, and each arm is are preferably about 3½ to 3⅝ inches long. Arms 46, 48 have first ends 46c, 48c, which are about 1⅜ to 1½ inches wide, connected to back 44 so that their top edges 46a, 48a are flush with top edge 44a of back 44. Arms 46, 48 taper from first ends 46c, 48c to second distal ends 46d, 48d. Second distal end 46d of arm 46 has a width of about 1³⁄₁₆ to 1¼ inches, and second distal end 48d of arm 48 has a width of about ⅞ to 1 inch.

Preferably, cup holder 40 is attached to bottom cup 24 by a synthetic material which adheres when pressed together, such as velcro. Separable fastener material a synthetic material having complementary parts which adhere to each other when pressed together and adapted for use as a closure fastener, such as hook and loop-type separable fasteners. 90a is attached to bottom surface 42b of bottom 42 of cup holder 40, and separable fastener material 90b is attached to the outer bottom surface 24e of bottom cup 24. Cup holder 40 and bottom cup 24 are pushed together so that separable fastener material 90a on bottom surface 42b of bottom 42 of cup holder 40 engages separable fastener material 90b on outer bottom surface 24e of bottom cup 24. Thus, cup holder 40 is oriented as shown in FIG. 3, with its bottom 44 connected to bottom 24e of inverted bottom cup 24 through separable fastener material 90a, 90b, its back 44 extending perpendicularly upwardly from bottom 42 and elongated arms 46, 48 extending outwardly from back 44 and being parallel to bottom 42. Alternatively, cup holder 40 may be attached to bottom cup 24 by any other suitable means, such as adhesive glue.

Bottom surface 43a of cup holder insert 43 is attached to upper surface 42a of bottom 42 of cup holder 40, for example by an adhesive, to provide extra shock absorption during use. Cup holder insert 43 may be made of a coaster formed of rubber or any other suitable material. Alternatively, cup holder insert 43 may be formed from the bottom of a foam drink holder, described above. Preferably, cup holder insert 43 is formed from a planar disk of rubber, foam rubber or other suitable material having a diameter of about 2½ inches and a thickness of about ¼ to 5/16 inch. It may also include a circular opening 43c, for example where cup holder insert 43 is formed from the bottom of a foam drink holder.

Inner and outer surfaces 46e, 48e, 46f, 48f of arms 46, 48, respectively, are preferably covered with a synthetic material which adheres when pressed together, such as hook and loop-type separable fastener material 92. Thus, the width of the opening 13 at top end 12 of attachment 10 can be adjusted by wrapping arms 46, 48 together to form the desired width and pressing separable fastener material 92 on arms 46, 48 together to hold the arms 46, 48 in place at that desired width. This width can be easily adjusted to rearranging the engagement of arms 46, 48. This allows the wearer to adjust the width of opening 13 at top end 12 of attachment 10 to ensure a snug fit during use. Preferably when arms 46, 48 are covered with separable fastener material 92, the length of arm 46 including separable fastener material 92 is about 6 to 6¼ inches, and the length of arm 48 including separable fastener material 92 is about 4 to 4½ inches.

Top cup 30 can be formed from any container, such as a cup, and is preferably made of a flexible material, such as plastic or any other suitable material. It preferably has a thickness between about 1/16 and ⅛ inch. Top cup is oriented as shown in FIG. 3 so that its top edge 30a faces upwardly and its bottom 30d faces downwardly. Top cup 30 should be of sufficient height so that top edge 30a of top cup 30 is flush with top edge 44a of back 44 and top edges 46a, 48a of arms 46, 48 of cup holder 40 when top cup 30 is inserted in cup holder 40. Top cup 30 preferably has a height of about 2½ to 2⅝ inches and a diameter of about 2⅞ to 3 inches.

As an example, top cup 30 may be formed from a plastic cup, such as the shaker cup provided with Slim Fast® drink mixes. If this shaker cup is used, any portion of the shaker cup that extends beyond top edges 44a, 46a and 48a should be removed, for example by trimming with a hacksaw.

Figure 4:
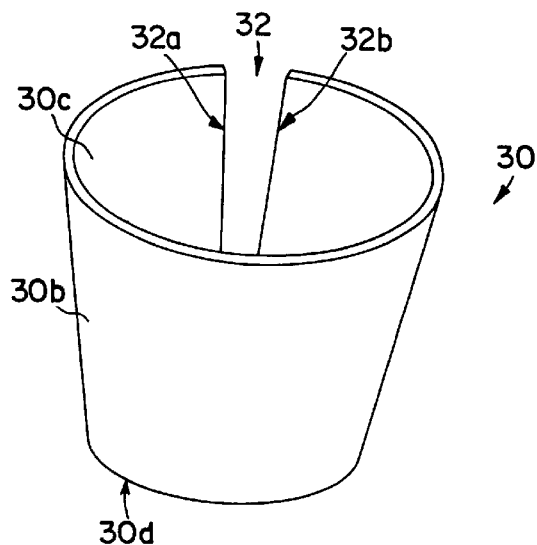
FIG. 4 is a perspective view showing the upper inner cup of the inventive athletic equipment attachment in a relaxed position.
Figure 5:
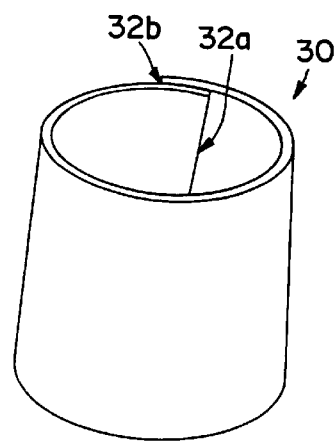
FIG. 5 is a perspective view showing the upper inner cup of the inventive athletic equipment attachment in a constricted position.

Preferably, a slit 32 is formed in side 30b of top cup 30. When top cup 30 is in a fully relaxed position as shown in FIG. 4, slit 32 is approximately ⅛ to ¼ inch wide. When top cup 30 is placed inside cup holder 40 and arms 46, 48 of cup holder 40 are adjusted to constrict top cup 30 and adjust the width of the opening 13 at top end 12 of attachment 10, side 30b of top cup 30 flexes and first and second sides 32a, 32b of slit 32 are drawn toward each other, and may overlap each other, as shown in FIG. 5. Thus, slit 32 allows the diameter of top cup 30 to be adjusted while the width of opening 13 at top end 12 of attachment 10 is adjusted by moving arms 46, 48 of cup holder 40. This provides a snug, adjustable fit for the wearer which allows the wearer to repeatedly insert, remove and reinsert his/her stump during use.

Next, bottom surface 52b of top cup insert 52 is attached to the inner bottom surface 31 of top cup 30 with adhesive glue or any other suitable means, so that top cup insert 52 is oriented as shown in FIG. 3 with its upper surface 52a facing upwardly and its bottom surface 52b facing downwardly and being pressed against inner bottom surface 31 of top cup 30. Top cup insert 52 is preferably formed from a planar disk of foam rubber or other cushioning material having a diameter of about 2½ inches. This provides cushioning for the end of the wearer's stump during use. As discussed above, top cup insert 52 may be formed from the bottom of a foam rubber drink holder. Preferably, top cup insert 52 has a central hole 53 formed therein and configured to engage the end of a particular wearer's stump to provide a comfortable, custom fit. Alternatively, top cup insert 52 may have an indentation on its upper surface 52a or may include raised sides, additional padding, or any other means to provide a custom fit for an individual wearer.

Preferably, inner side surface 30c of top cup 30 is padded with suitable padding material 80, such as cotton padding, foam rubber, or any other suitable material to provide a comfortable fit when a wearer's stump is inserted into top cup 30. Padding 80 may be attached to top cup 30 by any suitable means, such as adhesive glue, adhesive tape, or duct tape.

Preferably, a strip of synthetic material which adheres when pressed together, such as velcro 94 is attached to the upper outer surface 30b of top cup 30 so that velcro 94 will engage velcro 92 on the inner sides of arms 46, 48 of cup holder 40 when top cup 30 is inserted into cup holder 40 and arms 46, 48 are wrapped around top cup 30. Velcro 92 on inner surfaces 46e, 48e of arms 46, 48 will engage velcro 94 on top cup 30 when top cup 30 is inserted into cup holder 40. Top edge 94a of velcro strip 94 is preferably flush with upper edge 30a of top cup 30. Preferably, velcro strip 94 has a length of about 5 inches to cover a portion of the circumference of top cup 30 and a width of about 1 inch to engage velcro 92. Velcro strip 94 preferably does not extend to first and second sides 32a, 32b of slit 32 in top cup 30, so that first and second sides 32a, 32b easily overlap when cup 30 is constricted as described above.

Preferably, top cup 30 is attached to cup holder insert 43 by a synthetic material which adheres when pressed together, such as hook and loop-type separable fastener material. Velcro 91a is attached to outer bottom surface 30d of top cup 30 and separable fastener material 91b is attached to top surface 43a of cup holder insert 43, for example by an adhesive. Top cup 30 is inserted into cup holder 40 so that separable fastener material 91a on outer bottom surface 30d of top cup 30 engages separable fastener material 91b on top surface 43a of cup holder insert 43. Top cup 30 is oriented as shown in FIG. 3, with its outer bottom surface 30d attached to top surface 43a of cup holder insert 43 through separable fastener material 91a, 91b and its top edge 30a facing upwardly.

After top cup 30 is inserted into cup holder 40, material (not shown) such as duct tape, a sleeve made of polyvinyl chloride (PVC) or other material, or any other suitable material may be wrapped around the outside of top cup 30 and bottom 42 of cup holder 40 to secure top cup 30 to cup holder 40.

Top cup 30 and cup holder 40 are then inserted into cylinder 20 so that top edge 20a of cylinder 20 abuts bottom edges 46b, 48b of arms 46, 48 of cup holder 40. Top cup 30 and cup holder 40 are oriented within cylinder 20 as shown in FIGS. 2 and 3, with top edge 30a of top cup 30 and top edge 44a of back 44 of cup holder 40 facing upwardly, and bottom edges 46b, 48b of arms 46, 48 of cup holder 40 abutting top edge 20a of cylinder 20.

Top cup 30 and cup holder 40 may be inserted in cylinder 20 by spacing supports (not shown), such as tongue depressors, evenly around the outside of cup holder 40 and bottom cup 24, sliding cylinder 20 over bottom cup 24 and cup holder 40 up to bottom edges 46b, 48b of arms 46, 48 of cup holder 40, and then removing the supports once cylinder 20 is in place.

As discussed above, inverted bottom cup 24 is configured to engage handle 210 of equipment 200. When attachment 10 is connected to equipment 200, handle 210 of equipment 200 is inserted into opening 25 of inverted bottom cup 24. According to the first embodiment of the invention, the handle 210 of a piece of athletic equipment 200 is interchangeable, because it is removably attached to the bottom end 14 of attachment 10.

For example, a sheet of padding (not shown), such as ¼ inch thick compressed cotton padding, is folded to double thickness and attached to the inner side surface 24c of bottom cup 24. A synthetic material which adheres when pressed together, such as hook and loop-type fastener material (not shown) is then attached to the cotton padding and to the inner bottom surface 24d of bottom cup 24 by adhesive glue or any other suitable means, so that the entire inner side and bottom surfaces 24c, 24d of bottom cup 24 are covered with separable fastener material. The end and sides of handle 210 of equipment 200 are wrapped in separable fastener material (not shown), so that when handle 210 is inserted into bottom cup 24, the separable fastener material on handle 210 presses against the velcro on inner side and bottom surfaces 24c, 24d of bottom cup 24 to connect attachment 10 and handle 210 to each other. Separable fastener material may be connected to handle 210 by any suitable means, for example by securing the wrapped separable fastener material to itself, or by using clips, adhesive tape or adhesive glue. The cotton padding provides for a snug fit between the bottom cup 24 and handle 210, and the thickness of the cotton padding may be adjusted as necessary to ensure a snug fit.

As illustrated in FIG. 3, a silver pipe collar 106 may be opened, fitted around handle 210 where it meets the bottom end 14 of attachment 10 and secured to attachment 10 by any suitable means, such as duct tape. This provides additional support to attachment 10. Preferably, the pipe collar has a diameter of about 3½ inches, and a central hole 107 formed in the pipe collar has a diameter of about 1⅜ inches so that it fits around handle 210 of equipment 200. Such pipe collars are commercially available from Danco #60799 (a division of Plumbmaster, Inc. of Concordville, Pa. 19331).

Attachment 10 may also be reinforced and decorated by wrapping racket tape or other suitable material around the outer surface 21 of cylinder 20.

Another method of removably attaching attachment 10 to handle 210 of equipment 200 is through a conventional keyless chuck configuration such as that used in power drills to hold various drill bits. Such a keyless chuck device would be inserted in the bottom surface 24b of bottom cup 24 to receive handle 210 of equipment 200 when handle 210 is inserted into bottom cup 24.

Alternatively, attachment 10 may be removably attached to handle 210 of equipment 200 by any suitable means, such as a a tubular sleeve arrangement such as that described in U.S. Pat. No. 3,965,491 to Frenzel, a clamp such as that described in U.S. Pat. No. 3,747,128 to De Filipo, or a conventional snap-in arrangement, or any other suitable attachment means.

According to the second embodiment of the invention, handle 210 of athletic equipment 200 is permanently attached to the bottom end 14 of attachment 10 by any suitable means, including but not limited to any suitable combination of screws, clamps, adhesive, or other materials. For example, a cap 100 configured to be inserted inside bottom cup 24 may be attached to handle 210. Preferably, where the attachment is to be used with a field hockey stick, cap 100 is a cylindrical cap formed of wood or other suitable material having a height of about 1¾ to 2 inches and a diameter of about 2½ inches. A cylindrical indentation 101 having a height of about 1 to 1¼ inches and a diameter of about ¾ to 1 inch is formed in the center of cap 100, so that cap 100 has a thickness of about ⅜ to ½ inch and indentation 101 is capable of receiving handle 200 of equipment 210.

Handle 210 is inserted in indentation 101 of cap 100 so that cap 100 is oriented as shown in FIG. 3, with upper surface 100a of cap 100 facing upwardly and indentation 101 facing downwardly. Cap 100 and handle 210 are attached to each other and to attachment 10 by any suitable means. For example, fasteners 102, such as screws, may be inserted through first and second reinforcing pieces 60, 70, bottom cup 24, cap 100 and handle 210. Preferably, first reinforcing means 60 is a semi-rectangular block formed of wood or any other suitable material and having an inner curved surface 62 configured to engage outer surface 24 of bottom cup 20 and a planar outer surface 60a. First reinforcing means 60 preferably has a length of about 1½ to 1¾ inches, a height of about 1¼ to 1½ inches, and a width of about ⅝ to ¾ inch.

Second reinforcing means 70 preferably comprises a planar rectangular block formed of wood or any other suitable material and having upper and lower portions 71a, 71b and a planar inner surface 72 which is configured to abut planar outer surface 60a of first reinforcing means 60. Second reinforcing means 70 preferably has a length of about 5 to 5⅛ inches, a height of about ⅜ to ¼ inch, and a width of about 1 7⁄16 to 1½ inches. Cap 100, first reinforcing means 62 and second reinforcing means 70 are arranged so that their bottom edges 100b, 70b of cap 100 and second reinforcing means 70, respectively, are aligned with each other and with bottom edge 20b of cylinder 20 when assembled, and top edge 70a of second reinforcing means 70 is flush with top edge 44a of back 44 of cup holder 40. Bottom edge 60b of first reinforcing means 60 is raised upwardly about ½ to ¾ inch from bottom edge 70a of second reinforcing means 70 when attachment 10 is assembled, as shown in FIG. 2.

Figure 6:
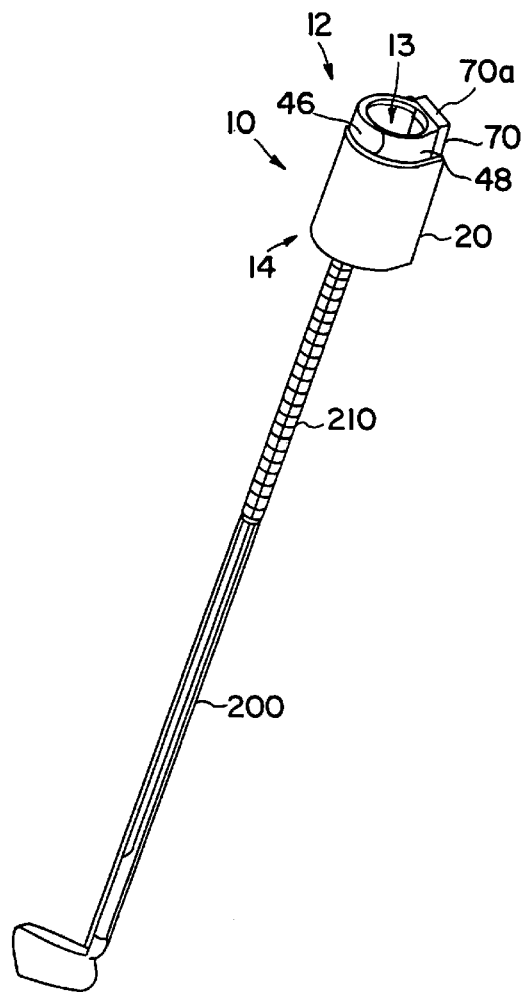
FIG. 6 illustrates the inventive athletic equipment attachment attached to a golf club.
Figure 8:
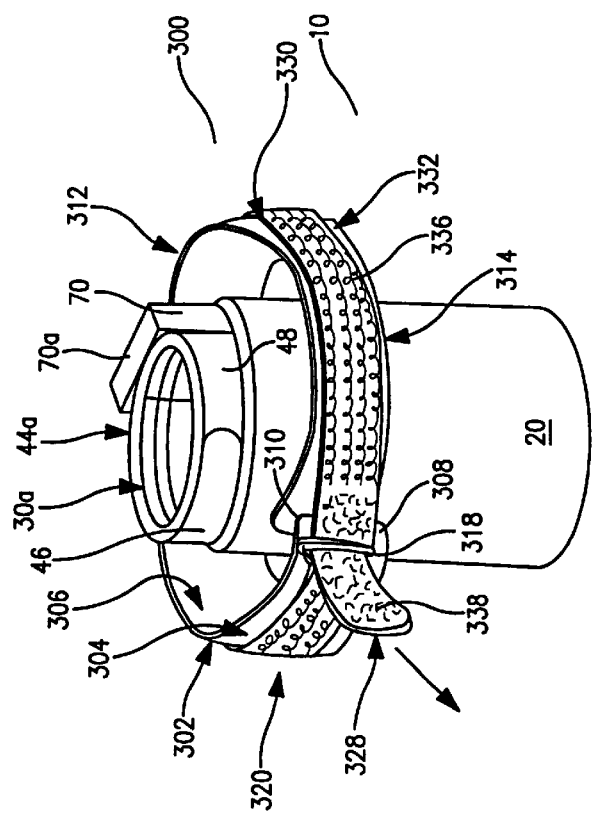
FIG. 8 is an exploded view of the inventive support strap and athletic equipment attachment.
Figure 7:
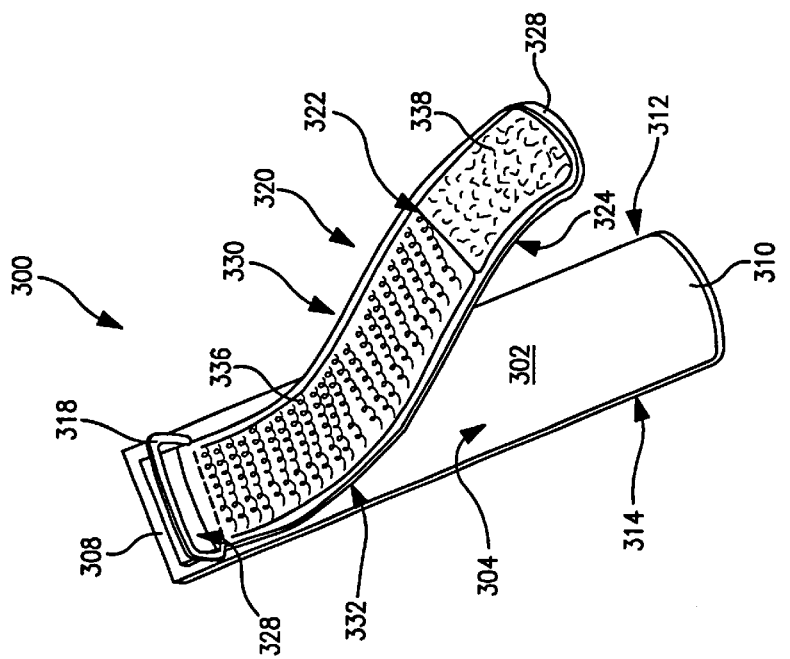
FIG. 7 is a perspective view showing the removable adjustable support strap.
Figure 9:
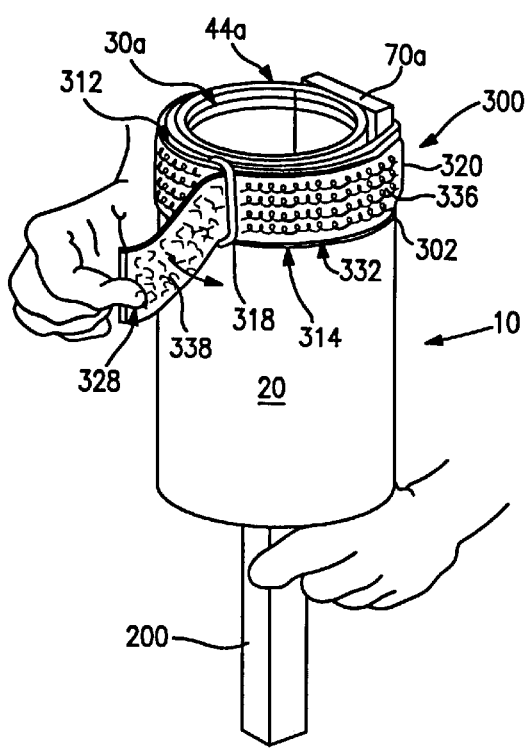
FIG. 9 illustrates placing the support strap around the athletic equipment attachment.

Fasteners 102, such as screws, can be inserted through bottom portion 71b of second reinforcing means 70, first reinforcing means 60, bottom cup 24, cap 100 and handle 210 to permanently affix attachment 10 to equipment 200. Cylinder 20 is then inserted around cup holder 40, bottom cup 24, and first and second reinforcing means 60, 70 as illustrated in FIG. 6. This embodiment is particularly desirable for use with golf clubs, as illustrated in FIG. 6, or any other applications where providing additional strength and support to the connection between attachment 10 and equipment 200 is desirable.

Upper portion 71b of second reinforcing means 70 may be attached to cup holder 40 by inserting fasteners 104, such as screws, through holes 41 formed in back 44 of cup holder 40 and through upper portion 71b of second reinforcing means 70.

Any other conventional means may be used to attach handle 210 to attachment 10 including but not limited to a threaded screw arrangement between handle 210 and attachment 10 such as that described in U.S. Pat. No. 4,661,113 to Adkins or U.S. Pat. No. 4,357,717 to Puhl.

According to a third embodiment of the invention, illustrated in FIGS. 7 through 11, a removable adjustable support strap 300 may be used in combination with attachment 10 to provide additional support to attachment 10. Support strap 300 can be formed from a commercially available counter-pressure band used to relieve pain and give support to patients having tennis elbow, such as the ELBOW POWER™ or EPIPOINT™ counter-pressure bands made by The Brace Center of Stephenville of Stephenville, Tex.

Support strap 300 preferably includes a rectangular strap 302 having a rectangular hook and loop-type separable fastener material strip 320 attached to the upper surface 304 of strap 302. Rectangular strap 302 has upper and lower surfaces 304, 306, first and second ends 308, 310 and upper and lower edges 312, 314. Rectangular strap 302 is preferably made of material having sufficient strength to reinforce attachment 10, such as neoprene. Preferably, rectangular strap 302 has a length of about 15½ inches and a width of about 2⅜ inches. A buckle 318 is attached to first end 302 of support strap 300 at its upper surface 304 and extends upwardly therefrom. Buckle 318 made be made of neoprene, plastic, metal, or any other suitable material.

Strip 320 has upper and lower surfaces 322, 324, first and second ends 326, 328 and upper and lower edges 330, 332. Preferably, separable fastener material strip has a length of about 16½ inches and a width of about 2 inches. First and second separable fastener material portions 336, 338 face upwardly from upper surface 322 of velcro strip 320. First separable fastener material portion 336 preferably has a length of about 13 inches and second separable fastener material portion 338 preferably has a length of about 3½ inches. Lower surface 324 of first end 328 of separable fastener material strip 320 is attached to the upper surface 304 of first end 308 of strap 302 so that lower surface 324 of strip 320 is adjacent upper surface 304 of strap 320 (see FIG. 8.)

Figure 10:
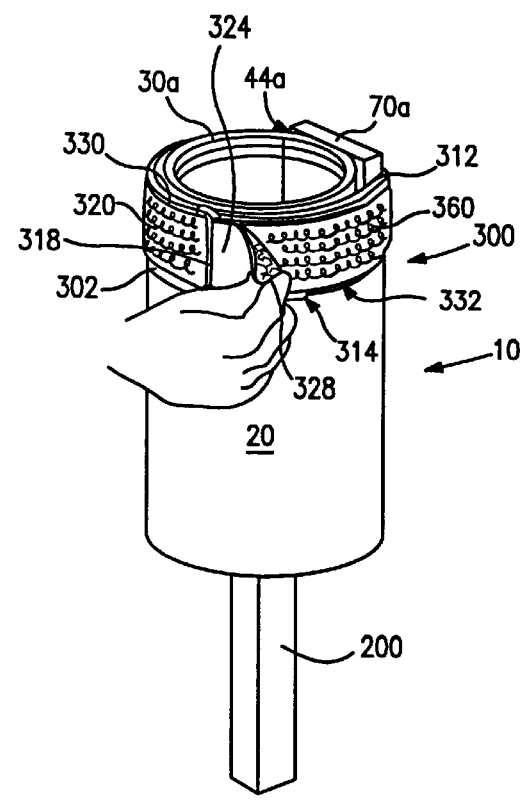
FIG. 10 illustrates securing the support strap around the athletic equipment attachment.
Figure 11:
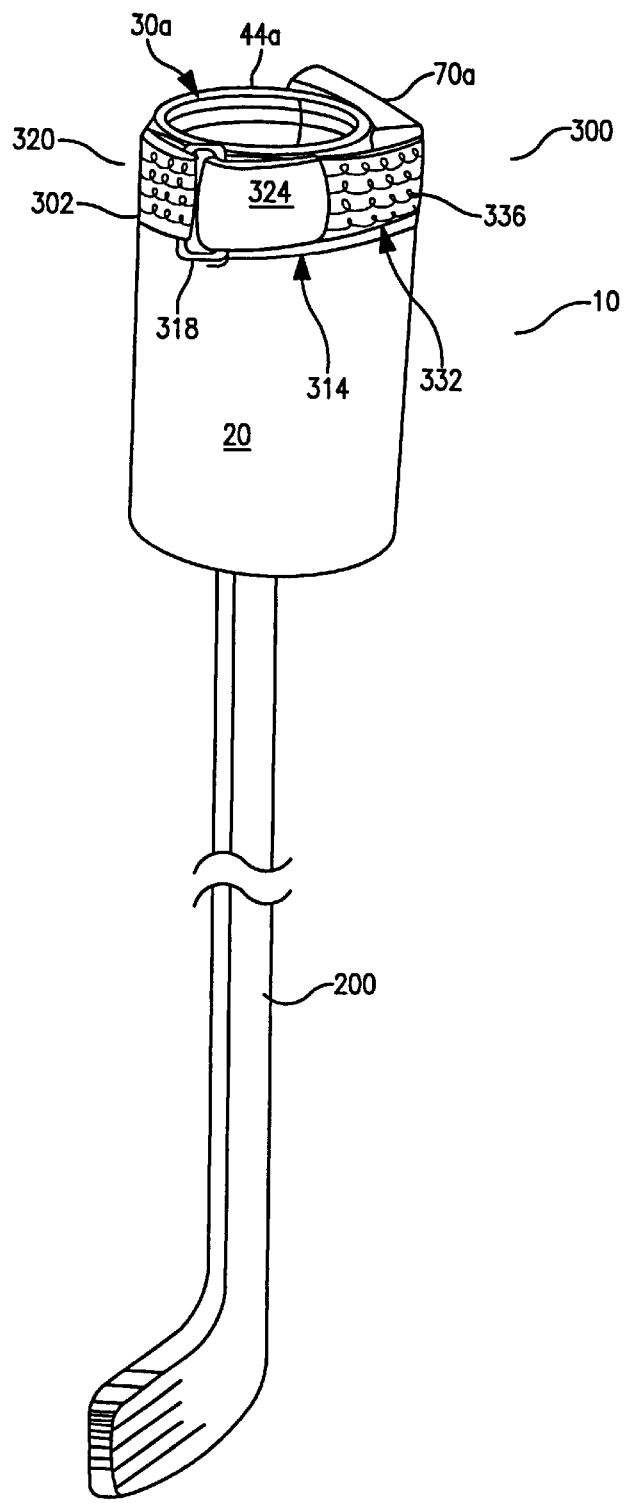
FIG. 11 illustrates the inventive athletic equipment attachment and support strap attached to a field hockey stick.
Figure 12:
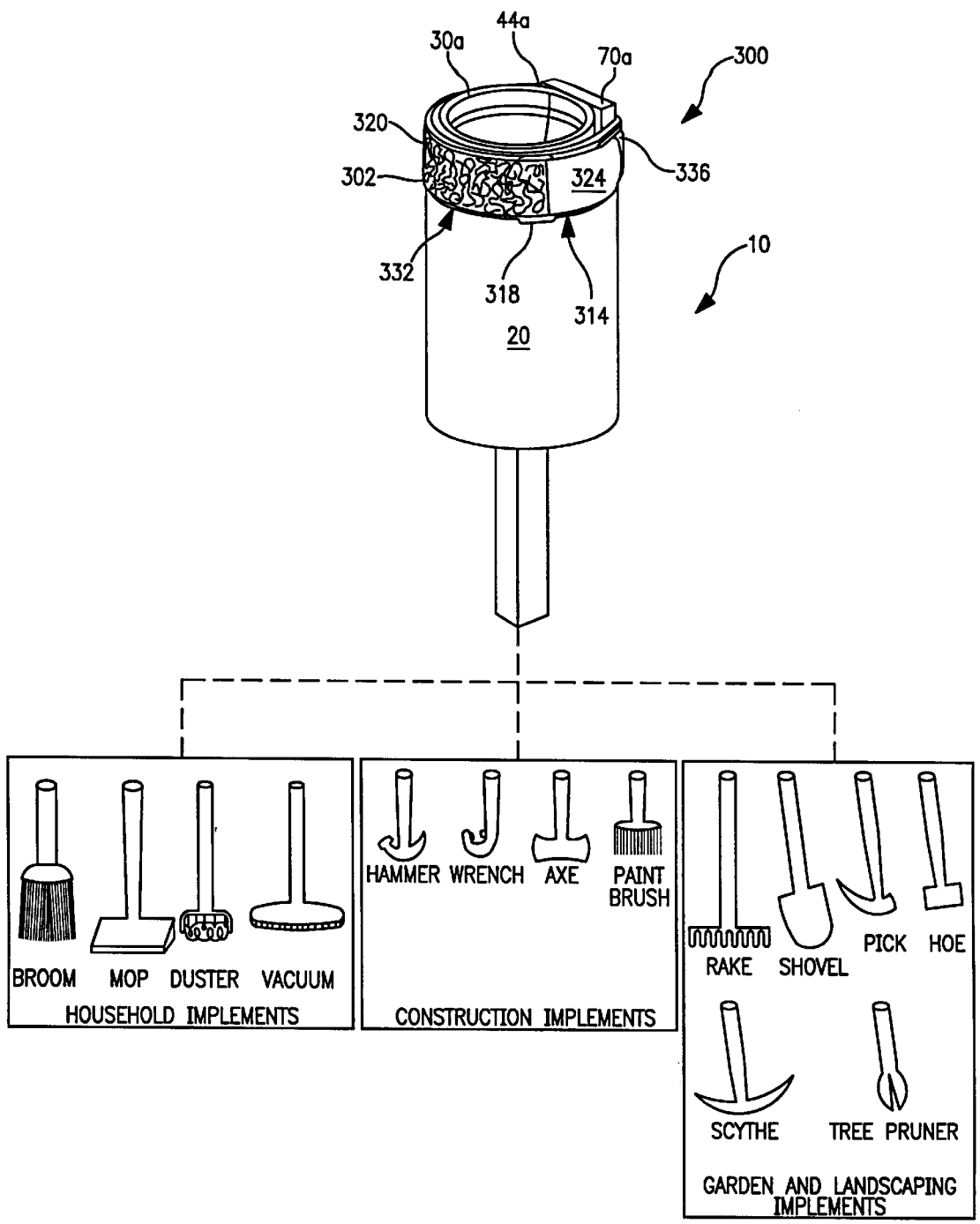
FIG. 12 illustrates use of the inventive athletic equipment attachment with household implements, construction implements and gardening and landscaping implements.

As shown in FIGS. 8 through 11, support strap 300 is used in combination with attachment 10 to provide additional support to attachment 10 as follows. Strap 300 is wrapped around the circumference of attachment 10 at its top end 12 so that lower surface 306 of strap 302 abuts outer surface 21 of cylinder 20; upper surfaces 304, 322 of strap 302 and separable fastener material strip 320, respectively, face outwardly from outer surface 21 of cylinder 20; upper edges 312, 330 of strap 302 and vertical strip 320, respectively, face upwardly; and lower edges 314, 332 of strap 302 and vertical strip 320, respectively, face downwardly. Second end 328 of separable fastener material strip 320 is inserted through buckle 318 and pulled back over buckle 318. Preferably, buckle 318 is located slightly off-center, as illustrated in FIGS. 10 and 11. This provides additional support for the adjustable opening 13 at top end 12 of attachment 10, defined by first and arms 46, 48, and strengthens the connection between separable fastener material 92 on first and second arms 46, 48. Support strap 300 is secured in place by pulling separable fastener material strip 320 tight around top end 12 of cylinder 20 and pressing second velcro portion 338 of separable fastener material strip 320 to first separable fastener material portion 336. Preferably, upper edge 312 of strap 302 is flush with top edge 30a of top cup 30 and top edge 44a of back 44 of cup holder 40 and, where support strap 300 is used with the second embodiment, top edge 70a of second reinforcing means 70, as illustrated in FIG. 11.

In addition to use as an athletic equipment attachment, attachment 10 can be adapted for use with conventional tools for everyday activities, such as household implements (for example, brooms, mops, dusters, vacuums), construction implements (for example, hammers, wrenches and other tools, axes, paint brushes), garden and landscaping implements (for example, rakes, shovels, picks, hoes, scythes, tree pruners), and any other hand-held implements.

Attachment 10 also has medical applications as a rehabilitation device for amputees or persons having congenital birth defects. For example, attachment 10 can be used in connection with weights for therapeutic applications.

Modifications and variations of the above-described embodiments of the present invention are possible, as appreciated by those skilled in the art in light of the above teachings. For example, cylinder 20, top cup 30, bottom cup 24 and cup holder 40 may be integrally formed of a single material, such as foam rubber or another suitable material, and any suitable adjusting means may be employed to provide an adjustable opening 13 at top end 12 of attachment 10.

It is therefore to be understood that, within the scope of the appended claims and their equivalents, the invention may be practiced otherwise than as specifically described.

What is claimed is:

1. A tool attachment for use by a person having a stump arm in connection with a tool having a handle, comprising:
   an outer container having a top end and a bottom end;
   an inner cup having an open top and a closed bottom to receive the stump arm, the inner cup being positioned within the outer container so that the top end of the outer container surrounds the open top of the inner cup;
   the inner cup having a slit running from the bottom of the inner cup to the open top of the inner cup to permit adjustment of the diameter of the open top;
   adjustable arms formed at the top end of the outer container and surrounding the open top of the inner cup for adjusting the diameter of the open top of the inner cup so that the person can remove the stump arm from the inner cup and reinsert the stump arm into the inner cup during use without changing the diameter of the open top of the inner cup; and
   said bottom end of the outer container having connecting means for connecting the attachment to the handle of the tool.

2. The attachment of claim 1, wherein the tool is a household implement.

3. The attachment of claim 1, wherein the tool is a construction implement.

4. The attachment of claim 1, wherein the tool is a gardening and landscaping implement.

5. The attachment of claim 1, further comprising a removable, adjustable support strap wrapped around said top end of said outer container of the attachment to provide support to the attachment.

6. The attachment of claim 1, wherein said bottom of said outer container is permanently connected to the handle of the tool.

7. The attachment of claim 1, for use in connection with a tool having a handle, wherein said connecting means removably connects the attachment to the handle of the tool.

8. The tool attachment of claim 1, wherein said inner cup is defined by a semi-rigid sidewall whereby the inner cup retains its shape and width during use to allow the person to remove the stump arm from the inner cup and reinsert the stump arm into the inner cup during use without readjusting the diameter of said opening.

9. An athletic equipment attachment for use by person having a stump arm, comprising:
   an outer container having a top end and a bottom end;
   an inner cup having an open top and a closed bottom to receive the stump arm, the inner cup being positioned within the outer container so that the top end of the outer container surrounds the open top of the inner cup;

the inner cup having a slit running from the bottom of the inner cup to the open top of the inner cup to permit adjustment of the diameter of the open top;

adjustable arms formed at the top end of the outer container and surrounding the open top of the inner cup for adjusting the diameter of the open top of the inner cup so that the person can remove the stump arm from the inner cup and reinsert the stump arm into the inner cup during use without changing the diameter of the open top of the inner cup; and said bottom end of the outer container having connecting means for connecting the attachment to the handle of the piece of athletic equipment.

10. The athletic equipment attachment of claim 9, further comprising a removable, adjustable support strap wrapped around said top end of said outer container of the attachment to provide support to the attachment.

11. The athletic equipment attachment of claim 9, wherein said bottom end of said outer container of the attachment is permanently connected to the handle of a piece of athletic equipment.

12. The athletic equipment attachment of claim 9, for use in connection with a piece of athletic equipment having a handle, wherein said connecting means removably connects the attachment to the handle of the piece of athletic equipment.

13. An athletic equipment attachment for use by a person having a stump arm, comprising:

a body having a length, an outer surface, a top end and a bottom end;

a reinforcing block having a top end and being connected to said outer surface of said body so that said top end of said reinforcing block is aligned with said top end of said body and said reinforcing block extends longitudinally downwardly along the length of said body so that said reinforcing block reinforces said body for use in connection with athletic equipment;

said top end of said body having an opening configured to receive the stump arm, the width of said opening being adjustable so that the person can remove the stump arm from said opening and reinsert the stump arm into said opening during use without adjusting the width of said opening;

first and second arms attached to the top end of said body and being configured to wrap around said outer surface of said body;

fastener means attached to said first and second arms for connecting said first and second arms when said first and second arms are wrapped around said outer surface of said body; said bottom end having connecting means for removably connecting the attachment to a handle of a piece of athletic equipment.

14. The athletic equipment attachment of claim 13, wherein said first and second arms have inner and outer surfaces, said ffurther comprising separable fastener material attached to said inner and outer surfaces of said first and second arms and separable fastener material attached to said outer surface of said body, wherein said separable fastener material on said first and second arms engages said separable fastener material on said outer surface of said body when said first and second arms are wrapped around said body.

15. The athletic equipment attachment of claim wherein said connecting means removably connects the attachment to the handle of the piece of athletic equipment.

16. A tool attachment for use by a person having a stump arm in connection with a tool having a handle, comprising:

a body having a length, an outer surface, a top end and a bottom end;

a reinforcing block having a top end and being connected to said outer surface of said body so that said top end of said reinforcing block is aligned with said top end of said body and said reinforcing block extends longitudinally downwardly along the length of said body so that said reinforcing block reinforces said body for use in connection with a tool;

said top end of said body having an opening configured to receive the stump arm, the width of said opening being adjustable so that the person can remove the stump arm from said opening and reinsert the stump arm into said opening during use without adjusting the width of said opening;

first and second arms attached to the top end of said body and being configured to wrap around said outer surface of said body;

fastener means attached to said first and second arms for connecting said first and second arms when said first and second arms are wrapped around said outer surface of said body;

said bottom end having connect means for connecting the attachment to the tool handle.

17. The attachment of claim 16, wherein said first and second arms have inner and outer surfaces, and further comprising separable fastener material attached to said inner and outer surfaces of said first and second arms and separable fastener material attached to said outer surface of said body, wherein said separable fastener material on said first and second arms engages said separable fastener material on said outer surface of said body when said first and second arms wrapped around said body.

18. The attachment of claim 16, wherein the tool is a household implement.

19. The attachment of claim 16, wherein the tool is a construction implement.

20. The attachment of claim 16, wherein the tool is a gardening and landscaping implement.

21. The attachment of claim 16, wherein said connecting means removably connect the attachment to the handle of the tool.

* * * * *